United States Patent
Bautista (10) Patent No.: US 7,366,557 B2
(45) Date of Patent: Apr. 29, 2008

(54) FLOWER CATHETER

(75) Inventor: Richard Bautista, Rancho Cucamonga, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 409 days.

(21) Appl. No.: 10/704,295

(22) Filed: Nov. 7, 2003

(65) Prior Publication Data

US 2005/0101852 A1    May 12, 2005

(51) Int. Cl.
*A61B 5/04* (2006.01)
(52) U.S. Cl. ..................................... 600/372
(58) Field of Classification Search ........... 600/374; 606/41; 607/122
See application file for complete search history.

(56) References Cited

U.S. PATENT DOCUMENTS

| | | | |
|---|---|---|---|
| RE34,502 E | 1/1994 | Webster, Jr. | |
| 5,282,845 A * | 2/1994 | Bush et al. ................. | 607/128 |
| 5,391,199 A | 2/1995 | Ben-Haim | |
| 5,443,489 A | 8/1995 | Ben-Haim | |
| 5,480,422 A | 1/1996 | Ben-Haim | |
| 5,531,686 A | 7/1996 | Lundquist et al. | |
| 5,546,951 A | 8/1996 | Ben-Haim | |
| 5,555,883 A | 9/1996 | Avitall | |
| 5,558,091 A | 9/1996 | Acker et al. | |
| 5,568,809 A | 10/1996 | Ben-haim | |
| 5,628,313 A | 5/1997 | Webster, Jr. | |
| 5,722,401 A | 3/1998 | Pietrowski et al. | |
| 5,722,402 A | 3/1998 | Swanson et al. | |
| 5,730,704 A | 3/1998 | Avitall | |
| 5,897,529 A | 4/1999 | Ponzi | |
| 5,897,554 A | 4/1999 | Chia et al. | |
| 5,928,228 A * | 7/1999 | Kordis et al. ................. | 606/41 |
| 6,024,739 A | 2/2000 | Ponzi et al. | |
| 6,064,905 A | 5/2000 | Webster, Jr. et al. | |
| 6,120,476 A | 9/2000 | Fung et al. | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,254,599 B1 * | 7/2001 | Lesh et al. .................. | 606/41 |
| 6,292,695 B1 | 9/2001 | Webster, Jr. et al. | |
| 6,330,473 B1 | 12/2001 | Swanson et al. | |
| 6,332,880 B1 | 12/2001 | Yang et al. | |
| 6,402,740 B1 | 6/2002 | Ellis et al. | |
| 6,542,781 B1 | 4/2003 | Koblish et al. | |
| 6,574,492 B1 | 6/2003 | Ben-Haim et al. | |
| 6,600,948 B2 | 7/2003 | Ben-Haim et al. | |

(Continued)

FOREIGN PATENT DOCUMENTS

EP    1 266 613 A1    12/2002

(Continued)

*Primary Examiner*—Lee S. Cohen
(74) *Attorney, Agent, or Firm*—Christie, Parker & Hale, LLP.

(57) ABSTRACT

A catheter having an elongated catheter body including a proximal end, a distal end and at least one lumen extending longitudinally therethrough is provided. A mapping assembly is mounted at the distal end of the catheter body and includes at least two loop shaped arms. Each arm includes two ends with a loop shaped portion extending therebetween. Both ends of each arm are mounted in the distal end of the catheter body. A plurality of electrodes are mounted on each arm.

20 Claims, 8 Drawing Sheets

U.S. PATENT DOCUMENTS

| | | |
|---|---|---|
| 6,652,515 B1 * | 11/2003 | Maguire et al. .............. 606/41 |
| 6,905,495 B1 * | 6/2005 | Fuimaono et al. ............ 606/41 |
| 2002/0133150 A1 | 9/2002 | Whayne et al. |
| 2002/0183638 A1 | 12/2002 | Swanson |
| 2003/0125614 A1 | 7/2003 | Fuimaono et al. |
| 2003/0171746 A1 | 9/2003 | Fleischman |
| 2004/0044277 A1 * | 3/2004 | Fuimaono et al. .......... 600/374 |
| 2006/0089634 A1 * | 4/2006 | Anderson et al. ............ 606/41 |

FOREIGN PATENT DOCUMENTS

| | | |
|---|---|---|
| WO | WO 95/02995 | 2/1995 |
| WO | WO 96/05768 | 2/1996 |
| WO | WO 97/24983 | 7/1997 |
| WO | WO 98/29033 | 7/1998 |

* cited by examiner

FLOWER CATHETER

FIELD OF THE INVENTION

The present invention relates to cardiovascular catheters and, in particular, to an improved catheter having at least two loop shaped arms each carrying a plurality of electrodes.

BACKGROUND OF THE INVENTION

Electrophysiology catheters are commonly used for mapping electrical activity in a heart. Electrophysiology is a specialty within the field of cardiology for diagnosis and treatment of electrical abnormalities of the heart. By mapping the electrical activity in the heart, ectopic sites of electrical activation or other electrical activation pathways that contribute to heart malfunctions may be detected. This type of information may then allow a cardiologist to intervene and destroy the malfunctioning heart tissues by targeted delivery of radio frequency energy. Such destruction of heart tissue is referred to as ablation, which is a rapidly growing field within electrophysiology and obviates the need for maximally invasive open heart surgery.

Attached to the electrophysiology catheters are electrodes, which are used to map, or collect electrical information about, the electrical activity in the heart. Such catheters are generally inserted percutaneously and fed through one or more major blood vessels into a chamber of the heart. A location sensor in the catheter, typically near the catheter's distal end, produces signals that are used to determine the position of the device relative to a frame of reference, such as a position external to the body or within the heart itself. The location sensor may be active or passive and may operate by generating or receiving electrical, magnetic or ultrasonic energy fields or other suitable forms of energy known in the art.

It would be desirable to provide a device that could easily and efficiently map the electrical activity in the heart to permit effective targeted radio frequency delivery to ablate malfunctioning heart tissue.

SUMMARY OF THE INVENTION

The present invention is directed to an improved catheter for mapping the electrical activity in a heart. The catheter includes at least two loop shaped arms at the distal end of the catheter, each having a plurality of electrodes. The arms are each capable of obtaining electrical, mechanical and/or locational data from points of interest within the heart. The arms allow for simultaneous mapping of multiple points within a region of interest in the heart, increasing the speed of mapping the region. The arms are designed to permit all of the exposed surface of the arms to simultaneously contact the heart tissue in and around the uniquely-shaped chambers of the heart.

In one embodiment, the invention is directed to a catheter having an elongated catheter body with a proximal end, a distal end and at least one lumen extending longitudinally therethrough. A mapping assembly is mounted at the distal end of the catheter body and includes at least two loop shaped arms. Each arm has two ends, both attached to the distal end of the catheter body, with a loop portion extending therebetween. A plurality of electrodes are attached to each arm.

In another embodiment, the invention is directed to a catheter having an elongated catheter body with a proximal end, a deflectable distal end and at least one lumen extending longitudinally therethrough. A mapping assembly is mounted at the distal end of the catheter body and includes at least two loop shaped arms. Each arm has two ends, each attached to the distal end of the catheter body with a loop portion extending therebetween. A plurality of electrodes are attached to each arm. The distal end of the catheter body includes a tip section having a plurality of arm lumens. Each end of each loop shaped arm is mounted in a corresponding one of the plurality of arm lumens. An irrigation tube extends through the catheter body including the tip section and has an open distal end in proximity to the loop shaped arms.

In yet another embodiment, the invention is directed to a method for mapping a region of the heart including introducing the distal end of a catheter according to the present invention into the region of the heart to be mapped; positioning the mapping assembly so that at least one electrode from each arm is in contact with heart tissue; recording electrical data from the heart tissue; repositioning the mapping assembly such that at least one electrode from each arm contact heart tissue at a different location; and recording electrical data from the heart tissue. This procedure is repeated until the area of heart tissue of interest has been mapped.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
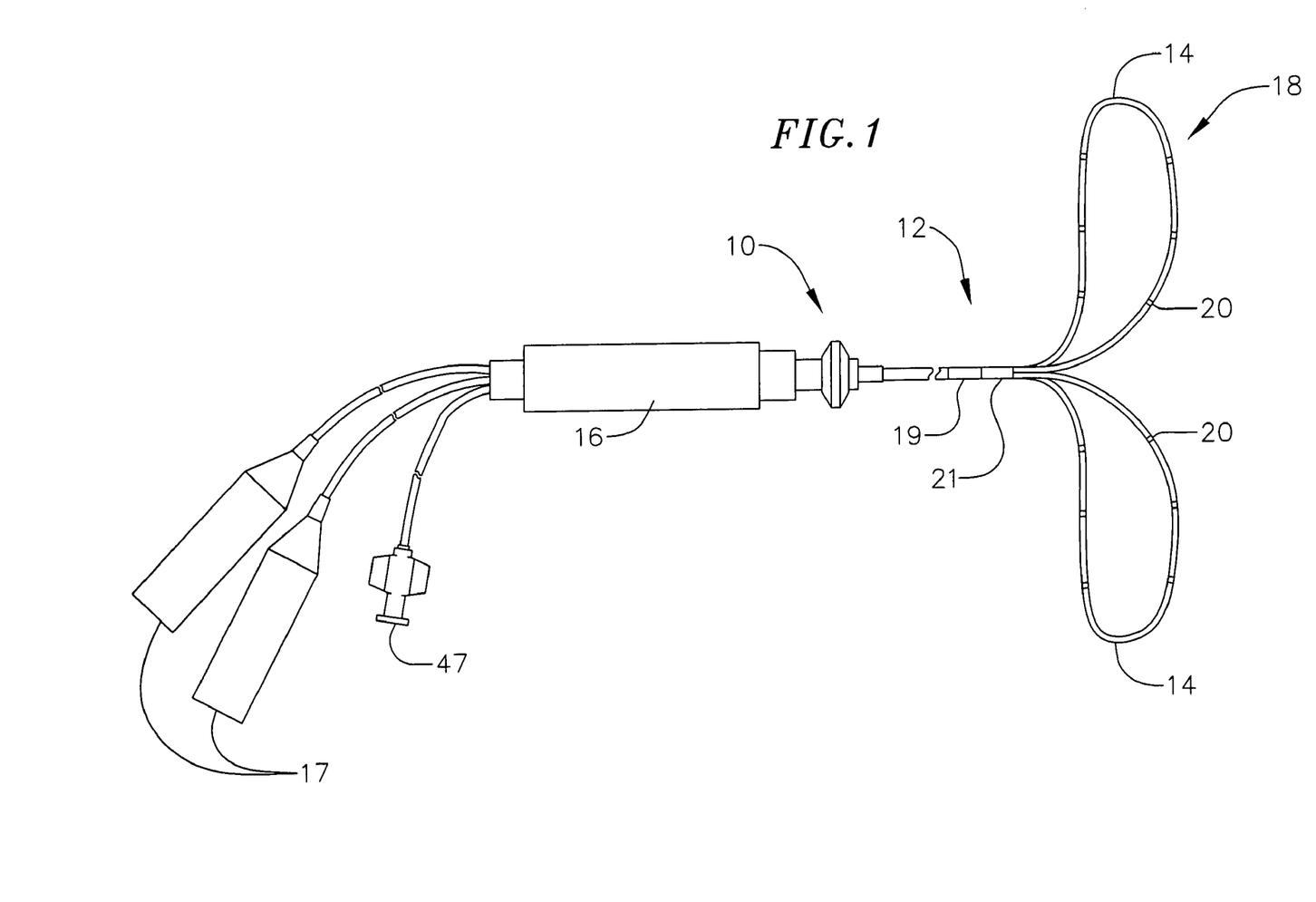
FIG. 1 is a perspective view of a catheter according to the invention.

The invention is directed to a catheter having a mapping assembly that includes at least two loop shaped arms. Each arm carries at least one electrode, such that when the arms are positioned in contact with heart tissue, each arm is capable of obtaining electrical data relevant to the heart tissue. As shown in FIG. 1, the catheter 10 comprises an elongated catheter body 12 having proximal and distal ends, a control handle 16 at the proximal end of the catheter body 12, and a mapping assembly 18 comprising at least two loop shaped arms 14 mounted at the distal end of the catheter body 12.

Figure 2:
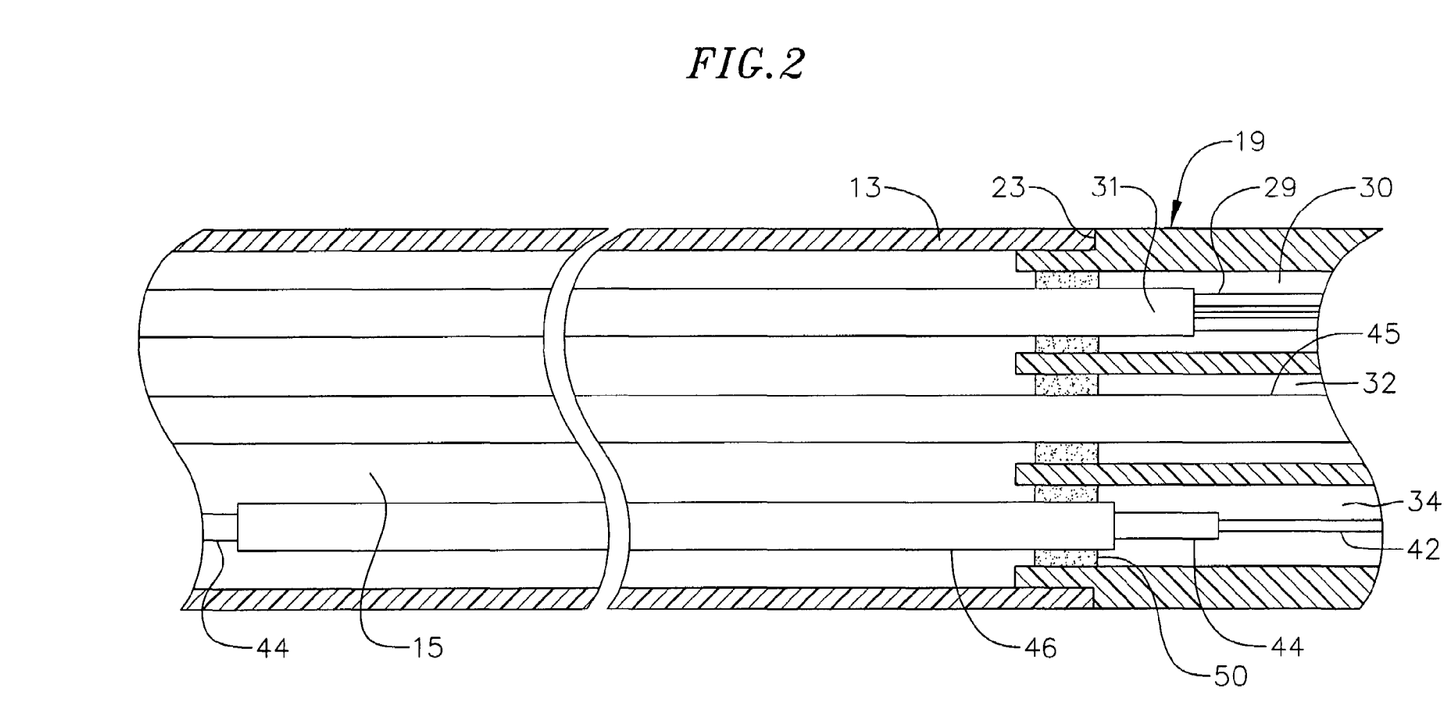
FIG. 2 is a schematic side cross-sectional view of a portion of the catheter of FIG. 1, showing a catheter body attached to a flexible tubing.

As shown in FIGS. 1 and 2, the catheter body 12 comprises an elongated tubular construction having, in this embodiment, a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 13 made of polyurethane or PEBAX® (polyether block amide). The outer wall 13 comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 13 is not critical, but is preferably thin enough so that the central lumen 15 can accommodate lead wires, puller wires, irrigation tubes, sensor cables and any other wires, cables or tubes. If desired, the inner surface of the outer wall 13 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

As shown in FIGS. 1 and 2, the distal end of the catheter body 12 preferably comprises a short length of flexible tubing 19, e.g. 2 to 4 inches in length, that is more flexible than the remainder of the catheter body 12. The flexible tubing 19 includes three lumens, namely a lead wire lumen 30 containing a protective sheath 31 that surrounds a plurality of lead wires 29, an irrigation lumen 32 containing an irrigation tube 45, and a puller wire lumen 34 containing a puller wire 42. The flexible tubing 19 is made of a suitable non-toxic material that is preferably more flexible than the remainder of the catheter body 12. A presently preferred material for the flexible tubing 19 is braided polyurethane, i.e., polyurethane with an embedded mesh of braided stainless steel or the like.

One means for attaching the flexible tubing 19 to the remainder of the catheter body 12 is illustrated in FIG. 2. The proximal end of the flexible tubing 19 comprises an outer circumferential notch 23 that is received by the inner surface of the outer wall 13 of the distal end of the outer wall 13. The flexible tubing 19 and the outer wall 13 are attached by glue or the like. Other arrangements for joining the flexible tubing 19 and the outer wall 13 are considered within the scope of the invention.

The catheter 10 also includes a mechanism for deflecting the distal end of the catheter body 12. As mentioned above, the puller wire 42 extends into the puller wire lumen 34 of the flexible tubing 19. The puller wire 42 is anchored at its proximal end to the control handle 16 and anchored at its distal end to the flexible tubing 19. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

In surrounding relation to the puller wire 42 is a compression coil. The compression coil 44 extends from the proximal end of the catheter body 12 to the proximal end of the flexible tubing 19. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. A Teflon® coating on the puller wire 42 allows it to slide freely within the compression coil 44. Along its length, the outer surface of the compression coil 44 is covered by a flexible, non-conductive protective sheath 46. The protective sheath 46 is preferably made of a polyimide tubing. The compression coil 44 is anchored at its proximal end to the proximal end of the catheter body 12 and at its distal end by glue from a glue joint 50 at the proximal end of the puller wire lumen 34.

Figure 3:
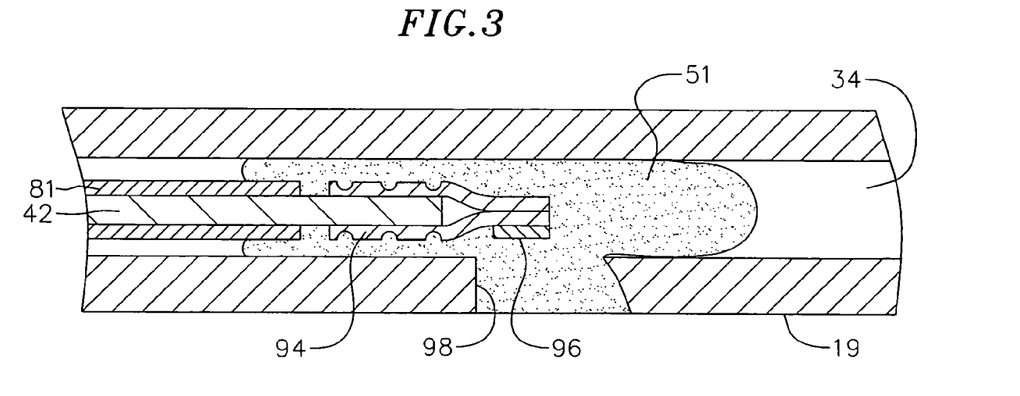
FIG. 3 is a side cross sectional view of a portion of the flexible tubing showing one means for attaching a puller wire therein.
Figure 4:
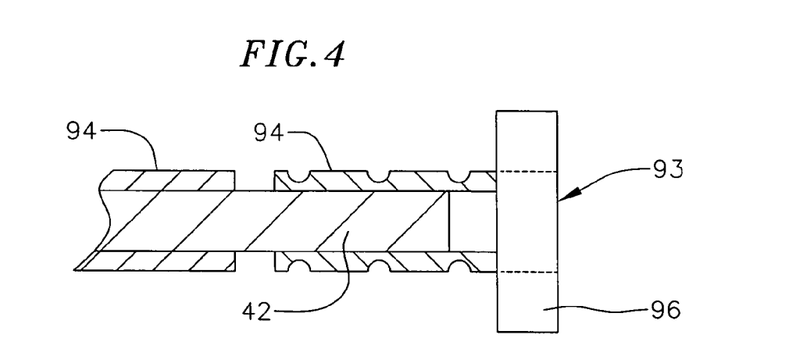
FIG. 4 is a top cross sectional view of a preferred puller wire anchor.
Figure 5:
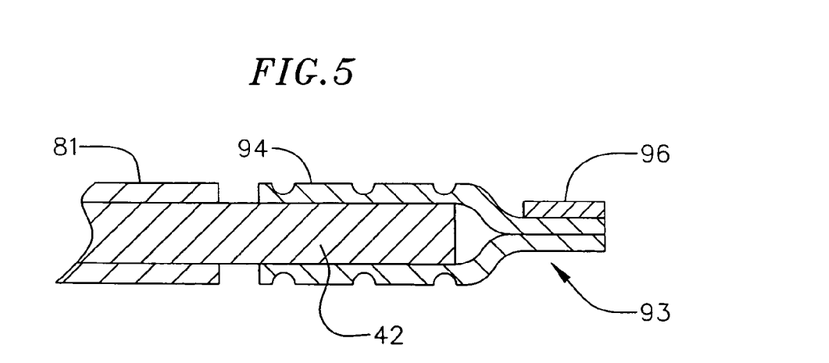
FIG. 5 is a side cross sectional view of the puller wire anchor of FIG. 4.

Preferably the puller wire 42 is anchored at its distal end to the side of the flexible tubing 19, as shown in FIGS. 3 to 5. In this embodiment, a T-shaped anchor 93 is formed which comprises a short piece of tubular stainless steel 94, e.g., hypodermic stock, which is fitted over the distal end of the puller wire 42 and crimped to fixedly secure it to the puller wire 42. The distal end of the tubular stainless steel 94 is fixedly attached, e.g., by welding, to a stainless steel cross-piece 96, such as stainless steel ribbon or the like. The cross-piece 96 sits in a notch 98 in a wall of the flexible tubing 19 that extends into the puller wire lumen 34. The stainless steel cross-piece 96 is larger than the notch 98 and, therefore, cannot be pulled through the notch 98. The portion of the notch 98 not filled by the cross-piece 96 is filled with glue 51 or the like, preferably a polyurethane glue, which is harder than the material of the flexible tubing 19. Rough edges, if any, of the cross-piece 96 are polished to provide a smooth, continuous surface with the outer surface of the flexible tubing 19. A Teflon® sheath 81, surrounds the puller wire 42 to prevent the puller wire 42 from cutting into the wall of the flexible tubing 19 when the distal end of the catheter body 12 is deflected.

Any other suitable technique for anchoring the puller wire 42 in the flexible tubing 19 can be used. Alternatively, other means for deflecting the distal end of the catheter body 12 can be provided, such as the deflection mechanism described in U.S. Pat. No. 5,531,686, the disclosure of which is incorporated herein by reference.

Longitudinal movement of the puller wire 42 relative to the catheter body 12, which results in deflection of the distal end of the catheter body 12, is accomplished by suitable manipulation of the control handle 16. Examples of suitable control handles for use in the present invention are disclosed, for example, in U.S. Pat. Nos. Re 34,502, 5,897,529 and 6,575,931, the entire disclosures of which are incorporated herein by reference.

If desired, the catheter can include two or more puller wires (not shown) to enhance the ability to manipulate the distal end of the catheter body 12. In such an embodiment, a second puller wire and a surrounding second compression coil extend through the catheter body 12 and into a second puller wire lumen (not shown) in the flexible tubing 19. Suitable control handles for use with a catheter having more than one puller wire are described in U.S. Pat. Nos. 6,123, 699, 6,171,277, and 6,183,463, the disclosures of which are incorporated herein by reference.

In the embodiment of FIG. 1, the mapping assembly 18 comprises two arms 14 each forming a loop. Each arm 14 includes two ends, both of which are attached to the distal end of the catheter body 12, such that the loop shaped portion of each arm 14 extends from the catheter body 12 to contact heart tissue. In one embodiment, each arm 14 extends in a plane transverse to the axis of the catheter body 12. Attaching both ends of each arm 14 to the catheter body 12 allows the loops of each arm 14 to apply a greater amount of pressure to the heart tissue in which it contacts than would be possible if only a single end of each arm 14 were attached to the catheter body 12. The length of the arm 14, and hence the size of the loops, can vary as desired. A length of about 2 cm is presently preferred.

Figure 9:
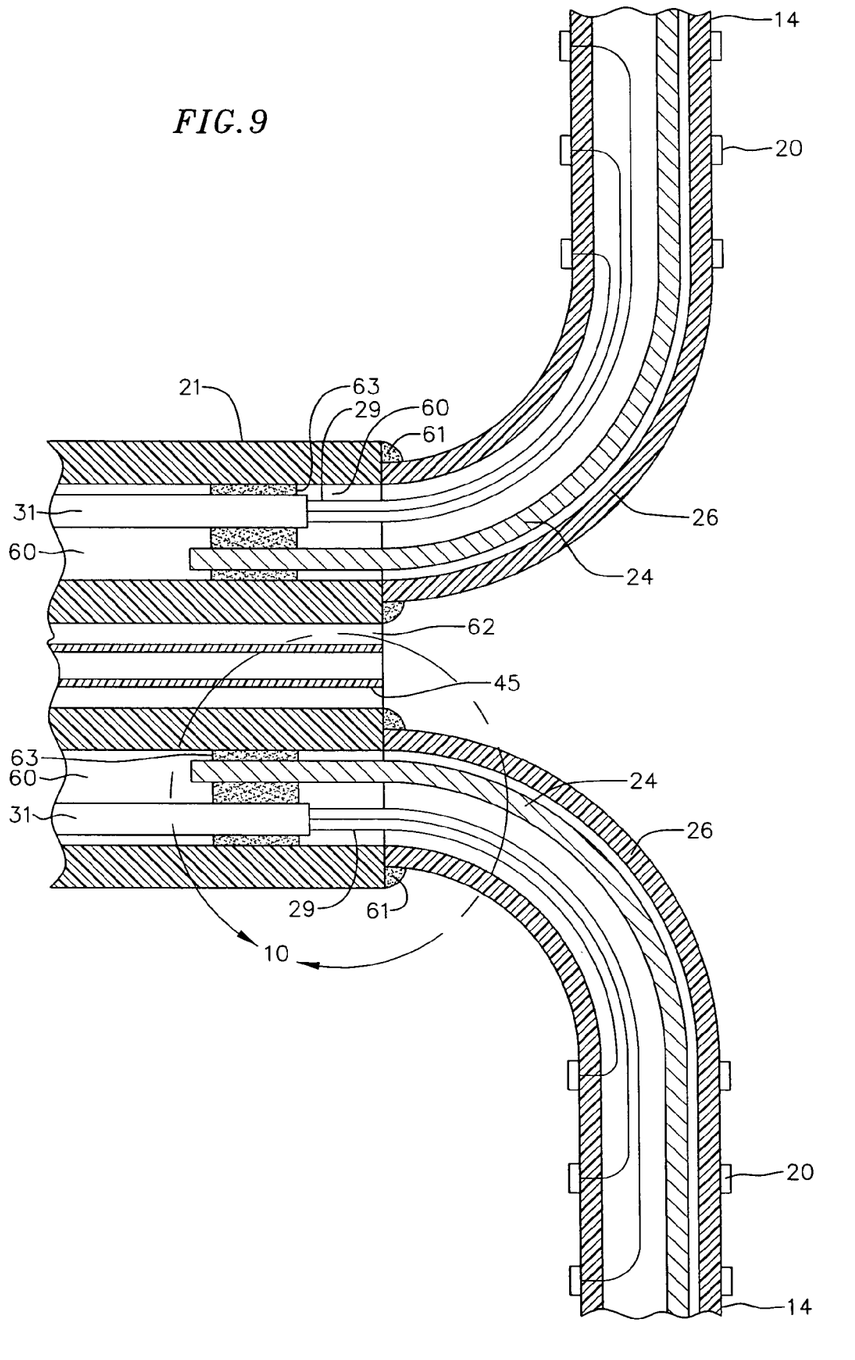
FIG. 9 shows a schematic side cross-sectional view of an attachment of a loop shaped arm of to the tip section.

As shown in FIG. 9, each arm 14 contains a supporting spine 24 comprising a metal or plastic material that has shape memory, such that, when bent or deflated by an applied force, the spine 24 will return to an initial, preformed shape when the force is removed. This characteristic enables the arms 14 to be bent into a generally linear collapsed configuration inside of a guiding sheath or the like and then return to their preformed, open, transverse configuration upon extending out of the guiding sheath. In a preferred embodiment, the spine 24 comprises a superelastic material, for example a nickel-titanium alloy, such as nitinol. Each arm 14 also comprises a non-conductive tubular sleeve 26 in surrounding relation to the spine 24. In a preferred embodiment, the non-conductive tubular sleeve 26 comprises a biocompatible plastic tubing, such as a polyurethane or polyimide tubing.

As will be recognized by one skilled in the art, the number of arms 14 can vary as desired depending on the particular application. Thus, although embodiments described and depicted herein refer to two arms 14, any appropriate number of arms 14 may be used. As described in more detail below, the arms 14 are moveable between an open configuration, wherein, for example, each arm 14 extends radially outwardly from the catheter body 12, and a collapsed arrangement, wherein, for example, each arm 14 is disposed generally along a longitudinal axis of the catheter body 12 so that the arms are capable of fitting within a lumen of a guiding sheath, as discussed further below.

Each arm 14 carries a plurality of electrodes 20 mounted along its length. In the depicted embodiment, each of the plurality of electrodes 20 is a ring electrode. Preferably, each of the plurality of electrodes 20 is mounted in spaced relation on a corresponding one of the non-conductive tubular sleeves 26. The distance between each electrode 20 preferably ranges from about 0.5 mm to about 2 mm. The number of the electrodes is not critical. In the embodiment shown in FIG. 1, each arm 14 includes six electrodes 20. It is understood, however, that in other embodiments, each arm 14 may include any appropriate number of electrodes 20, disposed in any desired relation along the arm 14 as desired. Likewise, the size of the electrodes is not critical, although it is preferred that the electrodes 20 have a length of up to about 2 mm, and more preferably from about 0.5 mm to about 1 mm.

Each electrode 20 is electrically connected to an electrode lead wire 29, which in turn is electrically connected to a connector 17. The connector 17 is connected to an appropriate mapping or monitoring system (not shown). Each electrode lead wire 29 extends from the connector 17, through the control handle 16, through the catheter body 12, and into the non-conductive tubular sleeve 26 of a corresponding arm 14 where it is attached to its corresponding electrode 20. Each lead wire 29, which includes a non-conductive coating over almost all of its length, is attached to its corresponding electrode 20 by any suitable method.

A preferred method for attaching a lead wire 29 to the electrode 28 involves first making a small hole through an outer wall of the non-conductive tubular sleeve 26. Such a hole can be created, for example, by inserting a needle through the non-conductive tubular sleeve 26 and heating the needle sufficiently to form a permanent hole. The lead wire 29 is then drawn through the hole by using a microhook or the like. The end of the lead wire 29 is then stripped of any coating and welded to the underside of the electrode 20, which is then slid into position over the hole and fixed in place with polyurethane glue or the like. Alternatively, each electrode 20 may be formed by wrapping the lead wire 29 around the non-conductive tubular sleeve 26 a number of times and stripping the lead wire of its own non-conductive coating on its outwardly facing surfaces. In such an instance, the lead wire 29 itself functions as the electrode 20.

An irrigation tube 45, preferably comprising a non-conductive material such as PEBAX, polyimide or polyurethane, may extend through the catheter body 12 and through the control handle 16 or out a sidearm (not shown) and terminate in a luer hub 47 or the like as is known in the art and, for example, as described in U.S. Pat. No. 6,120,476, the disclosure of which is incorporated herein by reference. As discussed further below, the irrigation tube 45 may be used to introduce irrigation fluid to the region between the arms 14, to avoid thrombus formation which might result in adverse events and difficulties in removing the catheter 10 from the patient.

The distal end of the irrigation tube 45 is preferably glued in place between the arms 14. As would be recognized by one skilled in the art, the irrigation tube 45 can comprise a plurality of structures that define a continuous path through the catheter body 12 and into the handle 16, including a combination of one or more lumens and one or more tubes.

Figure 6:
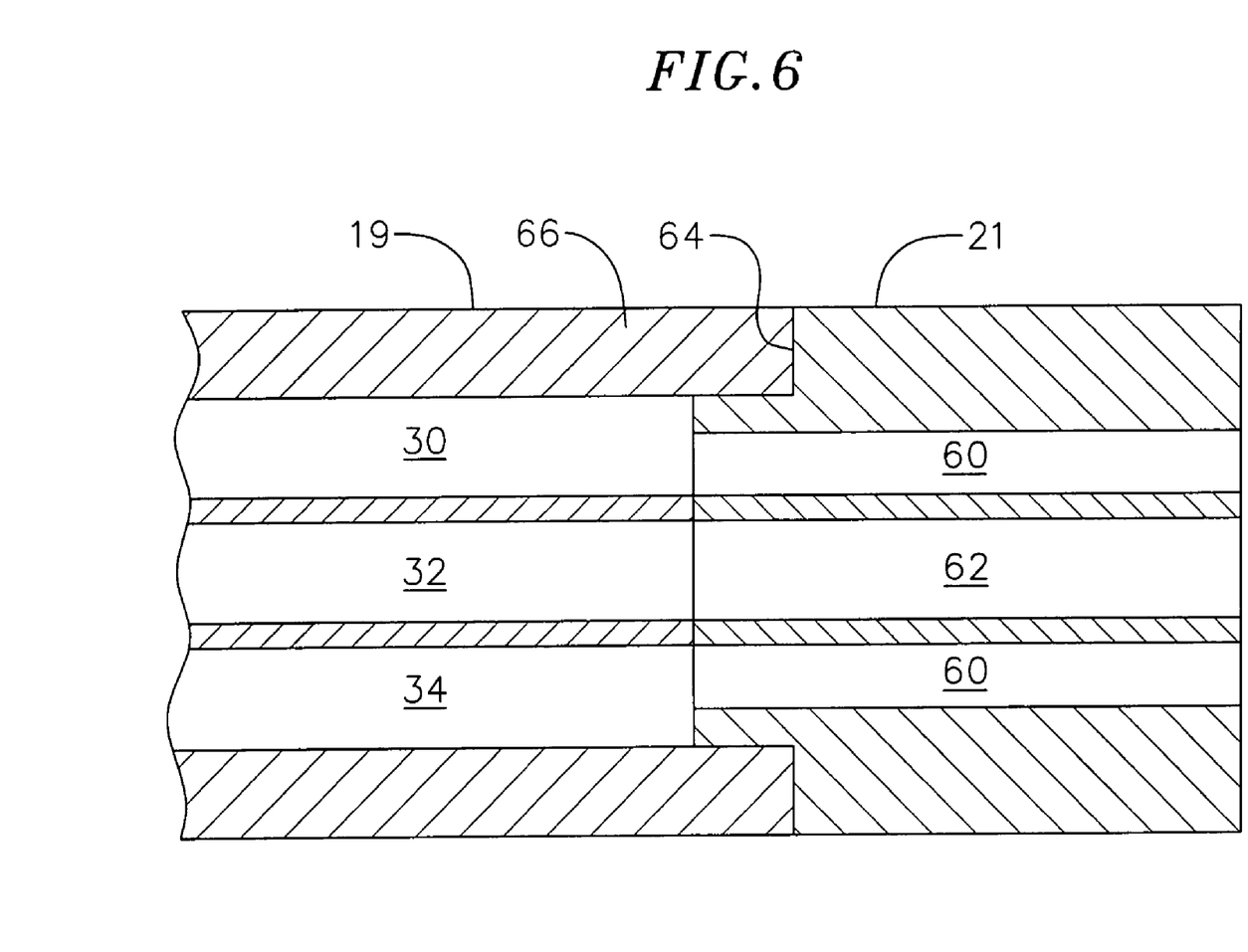
FIG. 6 is a schematic side cross-sectional view of a portion of the catheter of FIG. 1, showing the flexible tubing attached to a tip section.
Figure 7:
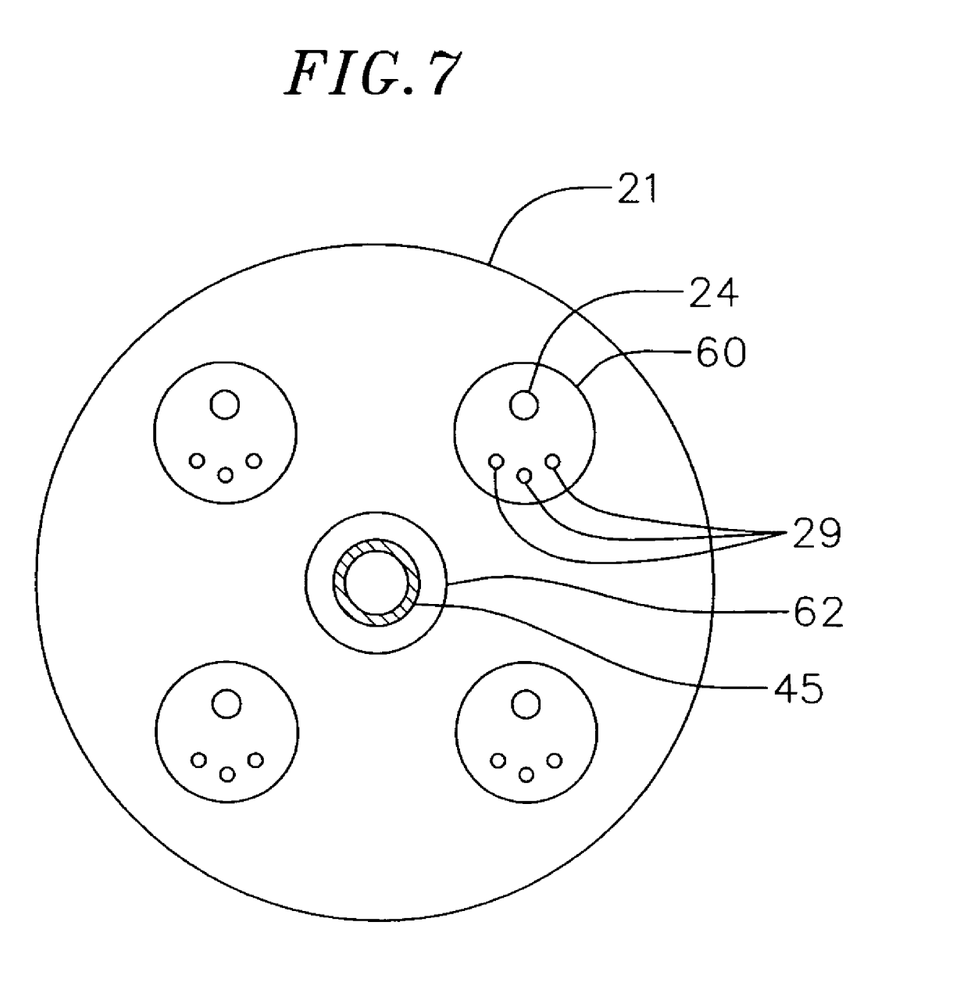
FIG. 7 shows a schematic end cross-sectional view of the tip section.
Figure 8:
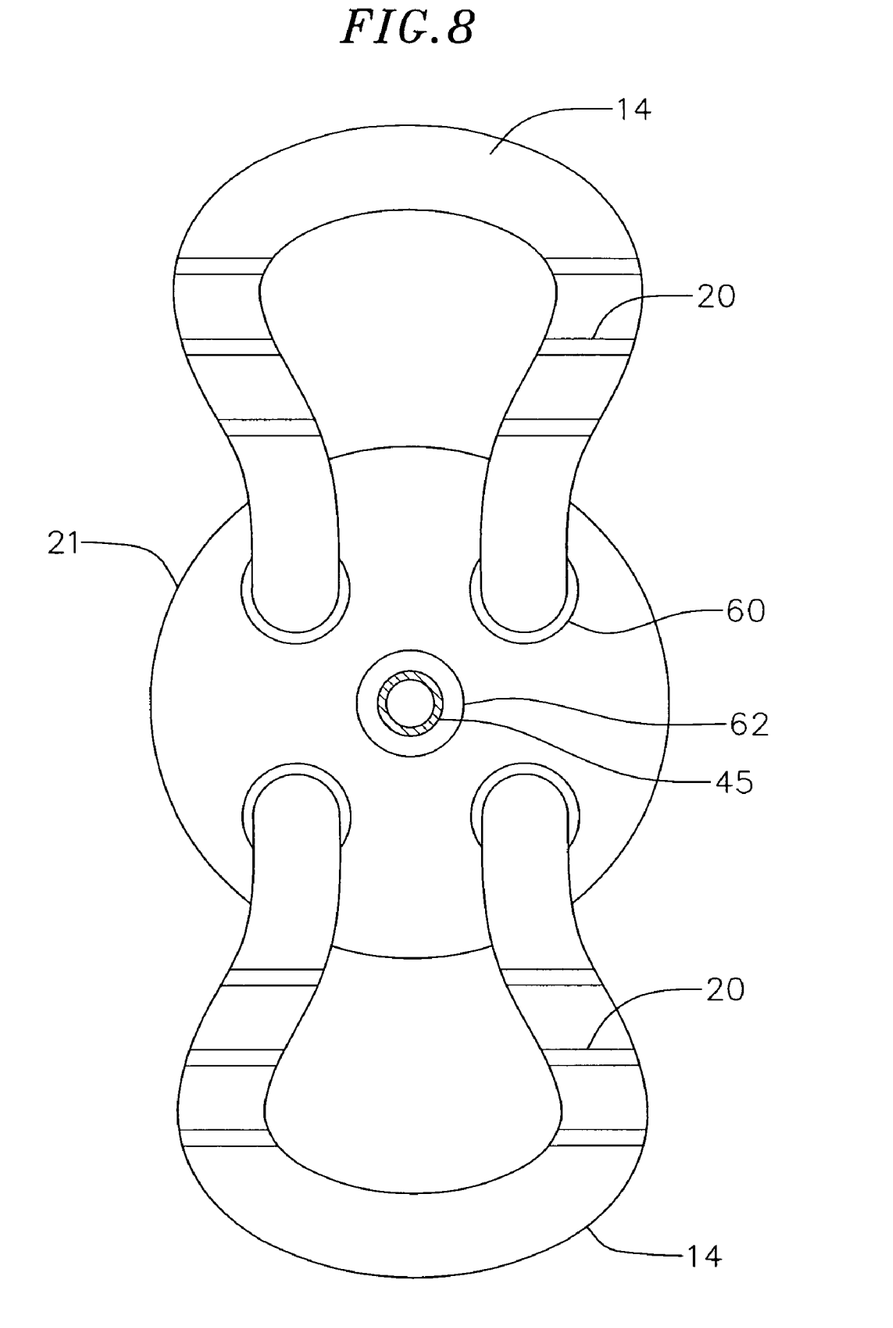
FIG. 8 shows a schematic end view of the catheter according to the present invention.

With reference to FIG. 6, a tip section 21 is mounted to the distal end of the flexible tubing 19. The tip section 21 provides a means for mounting the loop shaped arms 14 of the mapping assembly 18 to the catheter body 12. One means for attaching the tip section 21 to the flexible tubing 19 is illustrated in FIG. 6. The proximal end of the tip section 21 comprises an outer circumferential notch 64 that receives an inner surface of an outer wall 66 of the flexible tubing 19. The tip section 21 and the flexible tubing 19 are attached by glue or the like. Other arrangements for joining the tip section 21 and the flexible tubing 19 are considered within the scope of the invention.

As shown in FIGS. 7-10, the tip section 21 includes a plurality of arm lumens 60 and an irrigation lumen 62. The irrigation lumen 62 is preferable aligned with the irrigation lumen 32 of the flexible tubing 19. The irrigation lumen 62 of the tip section 21 contains the distal end of the irrigation tube 45.

Figure 10:
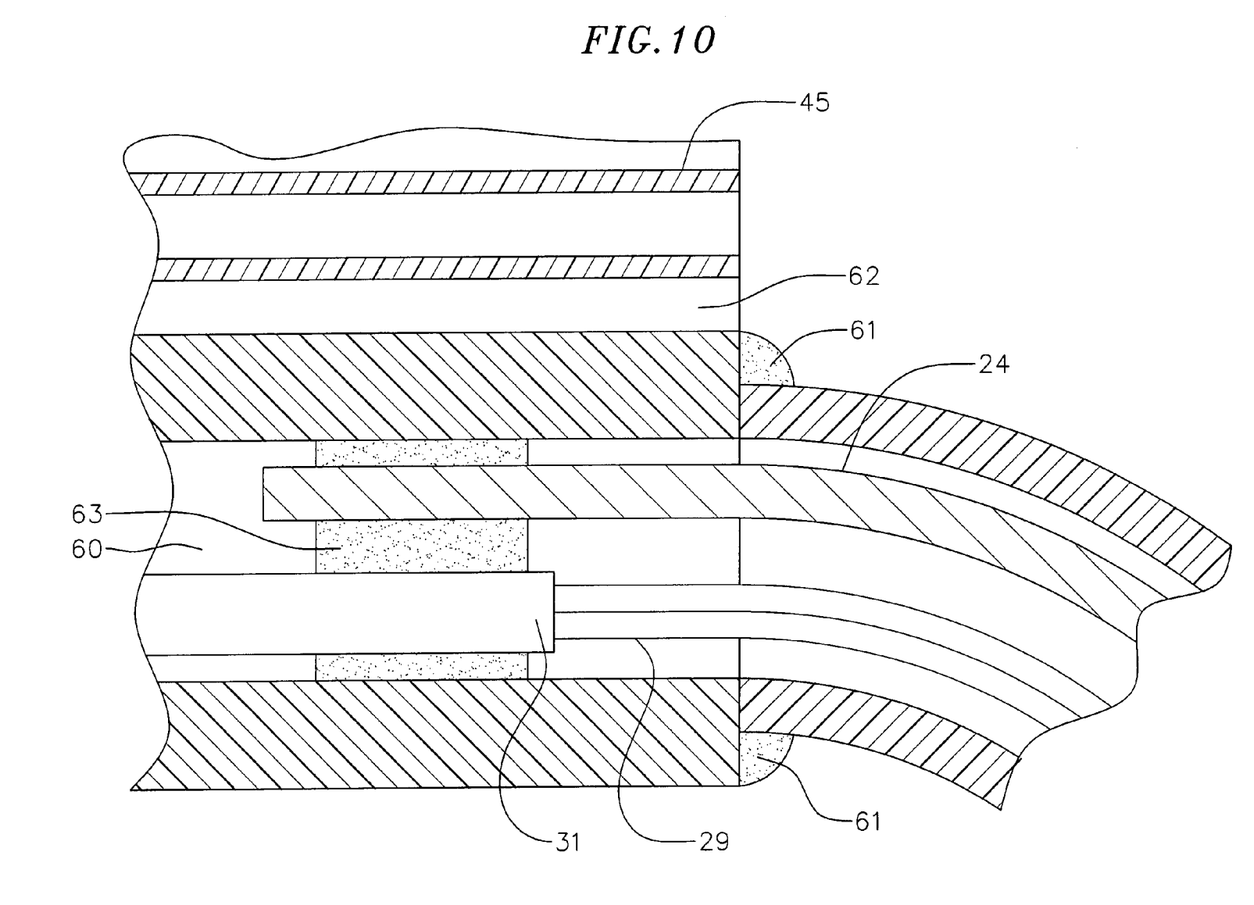
FIG. 10 is an enlarged view of a portion of FIG. 9.

One end of each arm 14 is mounted in a corresponding one of the arm lumens 60. This is accomplished by removing a portion of the non-conductive tubular sleeve 26 at the ends of each arm 14 to expose the spine 24. The exposed spine 24 is then inserted into a corresponding one of the arm lumens 60 until the end of non-conductive recovery butts against the distal end of the tip section 21. The ends of the spine 24 are then fixedly attached to the corresponding arm lumens 60 by any suitable means, such as with a polyurethane glue or the like. As shown in FIG. 10, the non-conductive tubular sleeve 26 forms a butt joint with the end of the tip section 21 and is attached thereat by glue 61 or the like. The spine 24 extends a short distance into the arm lumen 60, for example approximately 5 millimeters, and is attached therein, such as by a glue joint 63. The lead wire protective sheath 31 extends through the arm lumen 60, including through the glue joint 63. The lead wires 29 extend through the protective sheath 31, and are thus afforded longitudinal movement through the glue joint, and into the non-conductive tubular sleeve 26, where they are each attached to a correspondence electrode 20.

Preferably, each end of each arm 14 is mounted in a separate arm lumen 60. As such, in a preferred embodiment the tip section 21 includes two arm lumens 60 for each arm 14. However, in an alternative embodiment, both ends of each arm 14 may be mounted in the same arm lumen 60.

Mounting both ends of each arm 14 to tip section 21 allows the loop shaped portions of each arm 14 to apply a greater amount of pressure to the heart tissue in which it contacts than would be possible if only a single end of each arm 14 were attached to the catheter body 12.

As previously discussed, when mounting the spine 24 to the arm lumens 60, a portion of the non-conductive tubular sleeve 26 at the proximal end of each arm 14 is removed to expose the spine 24. Removing a portion of the non-conductive tubular sleeve 26 at the ends of each arm 14 enables the electrode lead wires 29 corresponding to each electrode 20 to extend from the arm lumen 60, and into each non-conductive tubular sleeve 26. As shown in FIG. 9, once inserted into the non-conductive tubular sleeves 26, the electrode lead wires 29 are electrically connected at their distal ends to their corresponding electrode 20.

Each arm 14 may also include at least one location sensor. The location sensor may be mounted at any location on the arm 14. Preferably a location sensor is mounted at about the midpoint of each arm. Each location sensor 30 is used to determine the coordinates of one or more electrodes 20 along the arm at each instant when the electrode 20 is being used to collect an electrical mapping data from the heart tissue. As a result, both electrical and locational data can be obtained for each data point that is mapped.

Each location sensor is connected to a corresponding sensor cable. Each sensor cable extends through the non-conductive tubular sleeve, catheter body 12 and control handle 16 and out the proximal end of the control handle 16 within an umbilical cord (not shown) to a sensor control module (not shown) that houses appropriate circuitry, as is well known in the art. Alternatively, the circuitry can be housed within the control handle 16, for example, as described in U.S. Pat. No. 6,024,739, the disclosure of which is incorporated herein by reference. Each sensor cable comprises multiple wires encased within a plastic covered sheath. In the sensor control module, the wires of the sensor cable are connected to the circuitry. The circuitry amplifies the signal received from the corresponding location sensor 30 and transmits it to a computer in a form understandable by the computer by means of a sensor connector at the proximal end of the sensor control module. Also, because the catheter 10 is designed for single use only, the circuitry preferably contains an EPROM chip that shuts down the circuitry approximately twenty-four hours after the catheter 10 has been used. This prevents the catheter 10, or at least the location sensors, from being used twice.

Preferably each location sensor is an electromagnetic location sensor. For example, each location sensor may comprise a magnetic-field-responsive coil, as described in U.S. Pat. No. 5,391,199, or a plurality of such coils, as described in International Publication WO 05768. The plurality of coils enables the six-dimensional coordinates (i.e. the three positional and the three orientational coordinates) of the location sensor to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480, 422, 5,546,951, and 5,568,809, and International Publication Nos. WO 95/02995, WO 97/24983, and WO 98/29033, the disclosure of which are incorporated herein by reference. A particularly preferred location sensor is a single axis sensor having a length ranging from about 3 mm to about 7 mm, preferably about 4 mm, such as that described in the U.S. patent application Ser. No. 09/882,125 filed Jun. 15, 2001, entitled "Position Sensor Having Core with High Permeability Material," the disclosure of which is incorporated herein by reference. Smaller sensors are particularly desirable for use in the present invention because of the need to keep the diameters of the arms 14 small enough so that they all fit within the lumen of a guiding sheath.

To use the catheter 10 of the invention, a cardiologist or electrophysiologist introduces a guiding sheath and a dilator into the patient, as is generally known in the art, so that the distal ends of the sheath and dilator are in the region of the heart to be mapped. To insert the catheter 10 into the guiding sheath, the mapping assembly 18 must be in its collapsed arrangement, wherein each arm 14 is disposed generally along the longitudinal axis of the catheter body 12. A suitable guiding sheath for use in connection with the catheter 10 is the PREFACE™ Braided Guiding Sheath (commercially available from Biosense Webster, Inc., Diamond Bar, Calif.). Such a guiding sheath has sufficient strength to maintain each spine 24 in its collapsed arrangement, such that the arms 14 and also the entire remainder of the catheter 10 can travel within the guiding sheath, from an insertion point in the patient, through a vein or artery and to a desired location in the heart.

Once the distal end of the catheter 10 has reached the desired location, relative longitudinal movement between the catheter 10 and the guiding sheath can be initiated to allow at least a portion of each arm 14 to protrude from the guiding sheath. Preferably, the guiding sheath is withdrawn proximally relative to the distal end of the catheter to expose the arms 14. When each arm 14 protrudes from the guiding sheath, such that the guiding sheath no longer applies a compression force to each arm 14, the arms 14 expand to their open, generally transverse configuration, wherein, e.g., each arm 14 extends radially outwardly from the catheter body 12, due to the shape memory of the spines 24.

In their open configuration, one or more of the plurality of electrodes 20 from each arm 14 can be placed into contact with the heart tissue such that electrical information can be obtained from the contacted heart tissue. The arms 14 can then be repositioned to contact a second heart tissue site such that electrical information can be obtained from that location. This process can be repeated until the heart has been satisfactorily mapped.

After mapping is completed, the catheter is moved proximally relative to the guiding sheath to retract the arms 14 within the guiding sheath. During mapping, care must be taken to avoid thrombus formation in the region between the arm 14 which can make it difficult to withdraw the arms back into the guiding sheath. To minimize such thrombus formation, irrigation fluid may be introduced through the irrigation tube 45 before, during and/or after a mapping procedure to flush the region between the arms 14. Preferably irrigation is provided continuously during the procedure to minimize any potential blood clotting in the irrigation tube 45. Suitable irrigation fluids for use in connection with the invention include saline, heparinized saline and thrombolitica. Although the irrigation tube 45 is preferably positioned coaxial with the catheter body 12 so that it is mounted between each of the arms 14, other positions for the irrigation tube 45 at or near the distal end of the catheter can be used in accordance with the present invention.

It is understood that the open, generally transverse configuration of the arms 14 can take on various shapes. For instance, in one embodiment, the loop shaped portion of each arm 14 extends from the catheter body approximately perpendicular to the axis of the catheter body. In other embodiments, the loops can be at a preformed angle other than 90°. It is understood that, if desired, one loop could be a first angle relative to the axis of the catheter body and the other loop could be at an angle different from the first angle.

Using the inventive catheter 10 having at least two loop shaped arms 14, each having electrical mapping and locational sensing capabilities, the cardiologist can map local activation time and obtain voltage maps. This information can guide the cardiologist in providing therapy to the patient. For example, where the cardiologist finds regions of the heart that do not have mechanical activity, he or she can revascularize those regions using known techniques, such as gene therapy or transmyocardial revasularization. The inventive catheter 10 allows the cardiologist to map the heart more quickly than traditional catheters by measuring multiple points of data simultaneously.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention.

Accordingly, the foregoing description should not be read as pertaining only to the precise structures described and shown in the accompanying drawings, but rather should be read as consistent with and as support for the following claims, which are to have their fullest and fairest scope.

What is claimed is:

1. A catheter comprising:
   an elongated catheter body having a proximal end, a distal end and at least one lumen extending longitudinally therethrough;
   a mapping assembly mounted at the distal end of the catheter body comprising:
      at least two loop shaped arms, wherein each arm comprises two ends with a loop shaped portion extending therebetween, and wherein each end of each arm is fixedly attached to the distal end of the catheter body, the loop shaped portion of each arm being adapted to move independently of the loop shaped portion of the other arms; and
      a plurality of electrodes mounted to each arm.

2. The catheter of claim 1, further comprising an irrigation tube extending through the catheter body and having an open distal end that is in communication with the outside of the distal end of the catheter body, in a region between the loop shaped arms.

3. The catheter of claim 1, wherein the distal end of the catheter body is deflectable.

4. The catheter of claim 3, further comprising a puller wire that extends through the lumen of the catheter body and is anchored at its distal end to the distal end of the catheter body wherein movement of the puller wire in a proximal direction causes the distal end of the catheter body to deflect.

5. The catheter of claim 1, wherein the distal end of the catheter body comprises a tip section having a plurality of arm lumens and wherein each end of each loop shaped arm is mounted in a corresponding one of the plurality of arm lumens.

6. The catheter of claim 1, wherein each arm comprises a non-conductive tubular sleeve having a support spine disposed therein and wherein each support spine has shape memory.

7. The catheter of claim 6, wherein each support spine is made of a material having shape memory.

8. The catheter of claim 6, wherein each support spine comprises nitinol.

9. The catheter of claim 6, wherein the spines of the arms have a preformed configuration whereby the arms extend radially outwardly from the catheter body in an open configuration.

10. The catheter of claim 9, wherein the spines, when bent due to the application of a force, will return to their preformed open position when the force is removed.

11. The catheter of claim 1, wherein the mapping assembly is moveable between an open configuration, in which each arm extends radially outward from the catheter body at an angle transverse to the axis of the catheter body, and a collapsed configuration, in which each arm is disposed generally along a longitudinal axis of the catheter body.

12. The catheter of claim 11, wherein, in the open configuration, each arm extends substantially perpendicular to the longitudinal axis of the catheter body.

13. A method for mapping a region of the heart comprising:
   introducing the distal end of the catheter of claim 1 into the region of the heart to be mapped;
   positioning the mapping assembly so that at least one electrode from each arm is in contact with heart tissue;
   recording electrical data from the heart tissue;
   repositioning the mapping assembly such that at least one electrode from each arm contacts heart tissue at a second location; and
   recording electrical data from the heart tissue at the second location.

14. The method of claim 13, wherein the distal end of the catheter is introduced through a guiding sheath having a distal end positioned in the heart so that the arms of the mapping assembly are within the guiding sheath.

15. The method of claim 14, wherein said positioning and repositioning comprise moving the guiding sheath proximally relative to the mapping assembly to allow the arms of the mapping assembly to move to their open configuration.

16. A catheter comprising:
   an elongated catheter body having a proximal end, a deflectable distal end and at least one lumen extending longitudinally therethrough;
   a mapping assembly mounted at the distal end of the catheter body comprising:
      at least two loop shaped arms, wherein each arm comprises two ends with a loop shaped portion extending therebetween, and wherein both ends of each arm are fixedly mounted to the distal end of the catheter body, the loop shaped portion of each arm being adapted to move independently of the loop shaped portion of the other arms, each arm comprising a support spine having shape memory, a non-conductive tubular sleeve in surrounding relation to the support spine; and a plurality of electrodes mounted over the non-conductive sleeve, each electrode being connected by means of an electrode lead wire to an electrical connector, at the proximal end of the catheter body; and an irrigation tube extending through the catheter body and having an open distal end that is in communication with the outside of the distal end of the catheter body, in proximity to the loop shaped arms, wherein the distal end of the catheter body comprises a tip section having a plurality of arm lumens and wherein each end of each loop shaped arm is mounted in a corresponding one of the plurality of arm lumens.

17. The catheter of claim 16, wherein the distal end of the catheter body comprises a flexible tubing having a distal end of a puller wire attached thereto, and wherein proximal movement of the puller wire causes the distal end of the catheter body to deflect.

18. The catheter of claim 16, wherein each spine comprises nitinol.

19. The catheter of claim 16, wherein the mapping assembly is moveable between an open configuration, in which each arm extends radially outward from the catheter body, and a collapsed configuration, in which each arm is disposed generally along a longitudinal axis of the catheter body.

20. The catheter of claim 19, wherein in the open configuration, each arm extends substantially perpendicular to the longitudinal axis of the catheter body.

* * * * *